United States Patent [19]

Loessel et al.

[11] Patent Number: 4,621,204
[45] Date of Patent: Nov. 4, 1986

[54] SENSOR INTEGRATOR SYSTEM

[75] Inventors: Mark C. Loessel, Mishawaka; Randall W. Miller, Goshen; Robert W. Myers, Mishawaka, all of Ind.

[73] Assignee: Miles Laboratories, Inc., Elkhart, Ind.

[21] Appl. No.: 634,574

[22] Filed: Jul. 26, 1984

[51] Int. Cl.⁴ .................. H03K 19/14; H03K 5/22; H03K 5/00
[52] U.S. Cl. .................... 307/311; 307/228; 307/494; 328/127
[58] Field of Search .......... 307/311, 228, 494; 328/127, 128

[56] References Cited

U.S. PATENT DOCUMENTS 3,913,022 10/1975 Kinoshita et al. ............ 328/127
4,320,521 3/1982 Balakrishnan et al. ........ 307/270
4,454,423 6/1984 Koob ............................ 328/127

Primary Examiner—Stanley D. Miller
Assistant Examiner—B. P. Davis
Attorney, Agent, or Firm—Roger N. Coe

[57] ABSTRACT

A sensor-integrator circuit having a sensor for producing a current varying in accordance with the sensed parameter or a reference current source, a comparator having inverting and noninverting inputs and an output and charge storage device coupled to the inverting input. The circuit is energized to obtain a given positive steady state reset voltage, a reference voltage is applied to the noninverting input of a comparator which is less positive than the steady state voltage and integration is initiated solely by alternately applying the current from the sensor and the reference current to the inverting input of the comparator.

4 Claims, 4 Drawing Figures

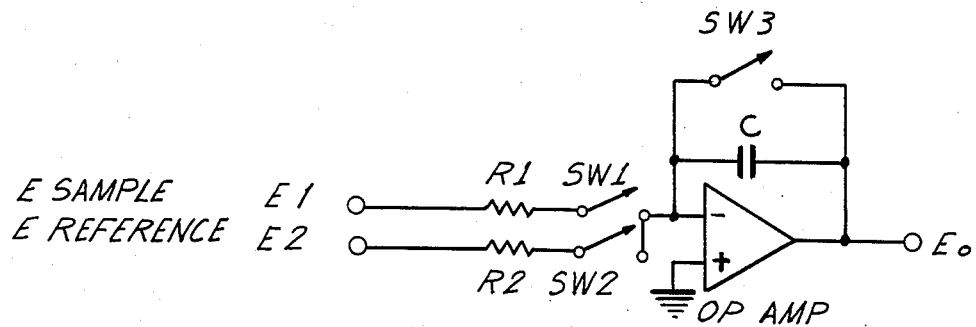
FIG. IA
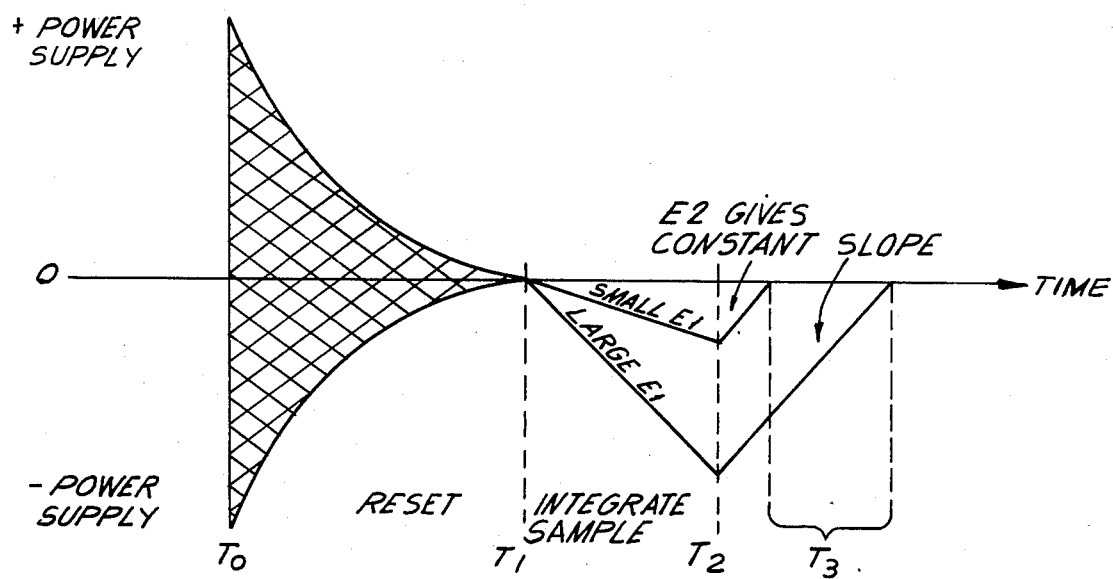
FIG. IB

SENSOR INTEGRATOR SYSTEM

BACKGROUND OF THE INVENTION

The present invention relates generally to a sensor integrator circuit and a method for converting a sensed parameter to a digital value with a dual slope integrator.

In particular, the present invention is directed to a system for converting sensed light to a digital value.

Prior art systems of this type are known and in particular a system of this type is described in U.S. Pat. No. 4,313,067, the contents of which are incorporated herein by reference.

While the system described therein is operable to obtain a time interval which corresponds to the light intensity sensed by a photo diode whereupon a digital value can be obtained from the time interval, the circuitry shown therein necessitates two or more control lines for carrying out this process.

SUMMARY OF THE INVENTION

The main object of the present invention is to provide an improvement over the prior art system wherein the sensor integrator system and the method of conversion can be carried out with a single control line.

Other objects and advantages of the present invention will become more apparent from the following detailed description of the invention when read in conjunction with the attached drawings which illustrate preferred embodiments thereof, wherein:

BRIEF DESCRIPTION OF THE DRAWINGS

FIG. 1A is a schematic of a classical integrator circuit;

FIG. 1B is a wave form diagram of the operation of a classical dual slope analog to digital converter utilizing the classical integrator;

DETAILED DESCRIPTION OF THE INVENTION

Figure 2A:
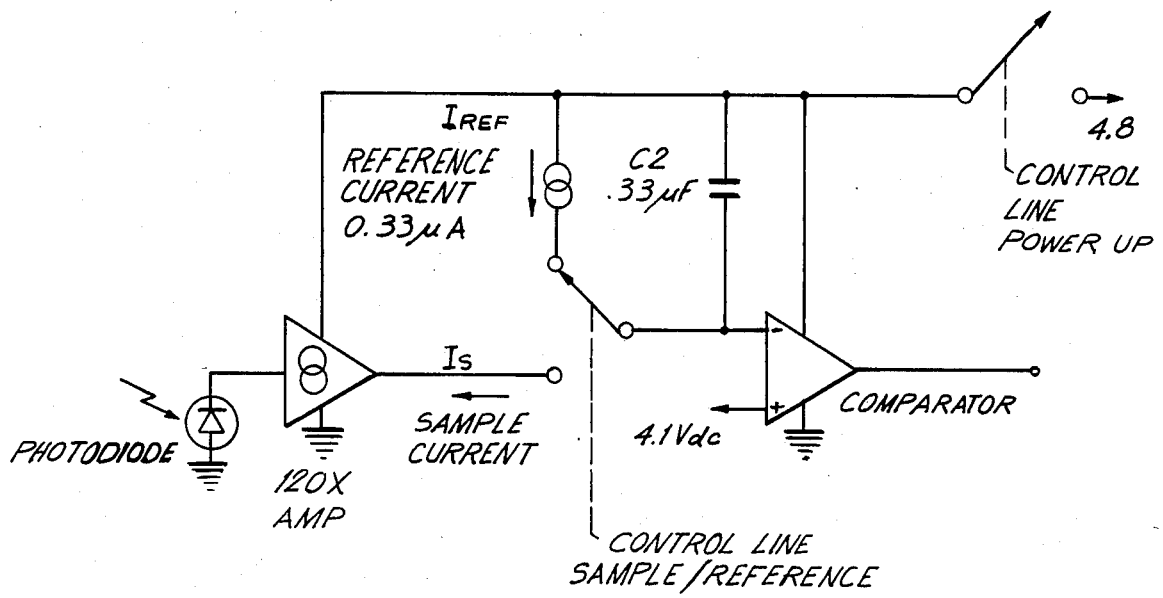
FIG. 2A is a schematic of the sensor-integrator circuit in accordance with the present invention.

Referring to FIG. 1A, in a classical integrator of the type shown therein, the integrator transfer function is $$E_o = \frac{-1}{RC} \int E_{in}\, dt.$$

To reset the integrator, switch SW3 is closed and the capacitor is shorted to 0 voltage. Therefore, $E_o$ goes to 0 volts. Assuming E1 is the sample voltage to be integrated, when switch SW1 is the only switch closed, the capacitor charges negatively. If the reference voltage E2 is to be integrated, than only switch SW2 is closed and the capacitor voltage increases in a positive direction.

FIG. 1B shows the results when a classical integrator of this type is used for the conventional type of dual slope A/D conversion. At time T0, the integrator is reset by closing SW3, whereupon $E_o$ is reset to the known condition of 0 volts. The starting voltage can be anywhere within the shaded area at T0 to T1. Since the switch shorts the capacitor (C), reset occurs quickly.

At T1, the sample is integrated by closing only switch SW1 and $E_o$ is determined in accordance with the aforementioned integrator transfer function. The sample voltage E1 is the unknown that is to be measured and the time interval T1–T2 is preset to be constant.

At time T2, switch SW2 is the only switch closed and the reference voltage E2 is integrated until the reset voltage is reached. The time interval from T2 until the reset voltage is reached is T3 and is a function of the sample voltage E1 in accordance with the following equations:

$$E1\,(T2 - T1) = E2\,(T3 - T2)$$

$$\frac{E1}{E2} = \frac{(T3 - T2)}{(T2 - T1)}$$

The circuits shown in the aforementioned U.S. Pat. No. 4,313,067 utilizes two of the three switches noted above to obtain this result and thus necessitates the use of two control lines to carry out the integration for A/D conversion.

The circuit in accordance with the present invention is a departure from the conventional dual slope integrator A/D converter in that it necessitates only a single control line and does not require a separate reset control in order to carry out successive A/D conversions.

The analog regulator is turned on for A/D conversions. Initially the analog regulator is off, and the capacitor is discharged. Since the voltage across a capacitor cannot change instantaneously, the voltage at both capacitor leads follows the analog regulator voltage, and the comparator is reset within the rise time of the regulator. The reset is accomplished in one millisecond. Selecting $I_{ref}$ maintains the reset state.

At time T1, the reference current is turned off and the sample current Is is selected. The sample current is then integrated for a fixed time interval during T1 to T2 and this time has been preselected as one second.

At time T2, the select control line is reversed and the reference current $I_{ref}$ is selected. The reference current is reverse integrated to the reset voltage at a constant slope. The time at which the reset steady state voltage is reached is signified by time T3 and the A/D conversion is carried out by taking the ratio of (T3−T2)/(T2−T1) which is the ratio of the sample current to the reference current. By using a crystal oscillator as the time reference, the number of pulses counted during time T3−T2 will be a digital representation of the sample current as all of the other elements in that ratio are known parameters.

Figure 2B:
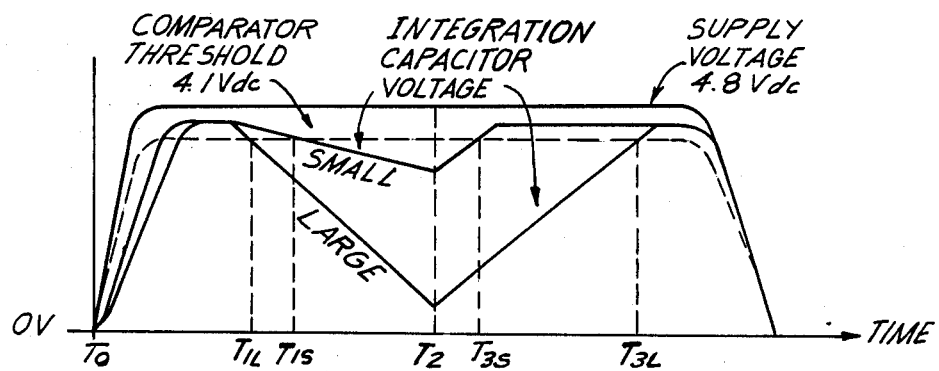
FIG. 2B is a wave form diagram of the operation of the circuit of FIG. 2A.

At time T4 (FIG. 2B), power can optionally be turned off for the circuitry to conserve the power consumption of the instrument. Thus the starting condition will be the same as at T0. Alternatively, if a delay to the reset condition is undesirable, the powering down can be eliminated. Thus at time T4 the circuit will be at its reset condition and ready for the next conversion corresponding to time T1.

If the initial state of the circuitry is unknown, reset can always be accomplished by selecting $I_{ref}$ for the time necessary to reverse integrate the maximum $I_{sp}$.

$$T\,\text{reset} \leq \frac{(4.1)(.33\ \mu F)}{.33\ \mu A} = 4.1\ \text{seconds}$$

It will be appreciated that the instant specification and claims are set forth by way of illustration and not limitation, and that various modifications and changes may be made without departing from the spirit and scope of the present invention.

What is claimed is:

1. A sensor-integrator circuit comprising:
   sensing means for producing a sample current to be integrated and which varies in accordance with a sensed parameter;
   a comparator having inverting and noninverting inputs, an output and a positive voltage supply input;
   charge storage means connected between the inverting input and the voltage supply input;
   means for applying a voltage to the voltage supply input and a reference current to the inverting input to produce a steady state positive voltage across the charge storage device;
   means for applying a reference voltage to the noninverting input of the comparator having a positive value less than and approximately equal to the steady state voltage; and
   control means for applying the sample current to the inverting input of the comparator instead of the reference current for a preselected known time period and thereafter applying the reference current to the inverting input.

2. The sensor integrator circuit according to claim 1, wherein the sensing means comprises a photodiode.

3. The sensor integrator circuit according to claim 2, wherein the charge storage means comprises a capacitor.

4. A method for converting a sensed parameter to a digital value comprising the steps of:
   converting the sensed parameter to a sample current varying in accordance with the sensed parameter;
   providing a comparator having inverting and noninverting inputs, an output and a positive voltage supply input;
   connecting a charge storage device between the inverting input and the voltage supply input;
   applying a voltage to the voltage supply input and a reference current to the inverting input until a steady state positive voltage is produced across the capacitor;
   applying a reference voltage to the noninverting input of the comparator having a value less than and approximately equal to the steady state voltage;
   applying the sample current instead of the reference current to the inverting input of the comparator for a preselected time interval whereby the voltage across the charge storage device drops below the reference voltage and the comparator output changes state and thereafter applying the reference current to the inverting input until the voltage across the change storage device reaches the steady state voltage and the comparator again changes state; and
   converting the time interval, from the end of the preselected time until the comparator again changes state, to a digital value.

* * * * *